United States Patent [19]

Torre

[11] 4,313,306
[45] Feb. 2, 1982

[54] LIQUIFIED GAS WITHDRAWAL APPARATUS

[76] Inventor: Douglas P. Torre, 7 Parkview Ave., Rowayton, Conn. 06853

[21] Appl. No.: 142,864

[22] Filed: Apr. 21, 1980

[51] Int. Cl.³ .............................................. F17C 7/02
[52] U.S. Cl. ................................. 62/51; 222/146 HA
[58] Field of Search ................................ 62/50, 51, 55; 128/303.1; 141/2, 3, 18, 82; 222/146 HA, 146 HE

[56] References Cited

U.S. PATENT DOCUMENTS 2,440,915  5/1948  Roehr ........................ 222/146 HA
4,037,631  7/1977  Schulze et al. ...................... 141/2
4,149,388  4/1979  Schneider et al. ..................... 62/50

Primary Examiner—Frederick R. Schmidt

[57] ABSTRACT

Apparatus for removing liquified gas which boils at ambient temperature from an enclosed reservoir. Removal from the reservoir is controlled by an on-off valve disposed in a delivery line, while selectively venting the pressurized vapor of the liquid generated above the reservoir. When flow is desired, the valve is opened and the vent is blocked by a warm heat rod slidable into and out of heat exchange relation with the liquid in the reservoir, which causes the liquid to boil and consequently, increases the vapor pressure on the liquid to cause it to flow through the delivery tube.

7 Claims, 7 Drawing Figures

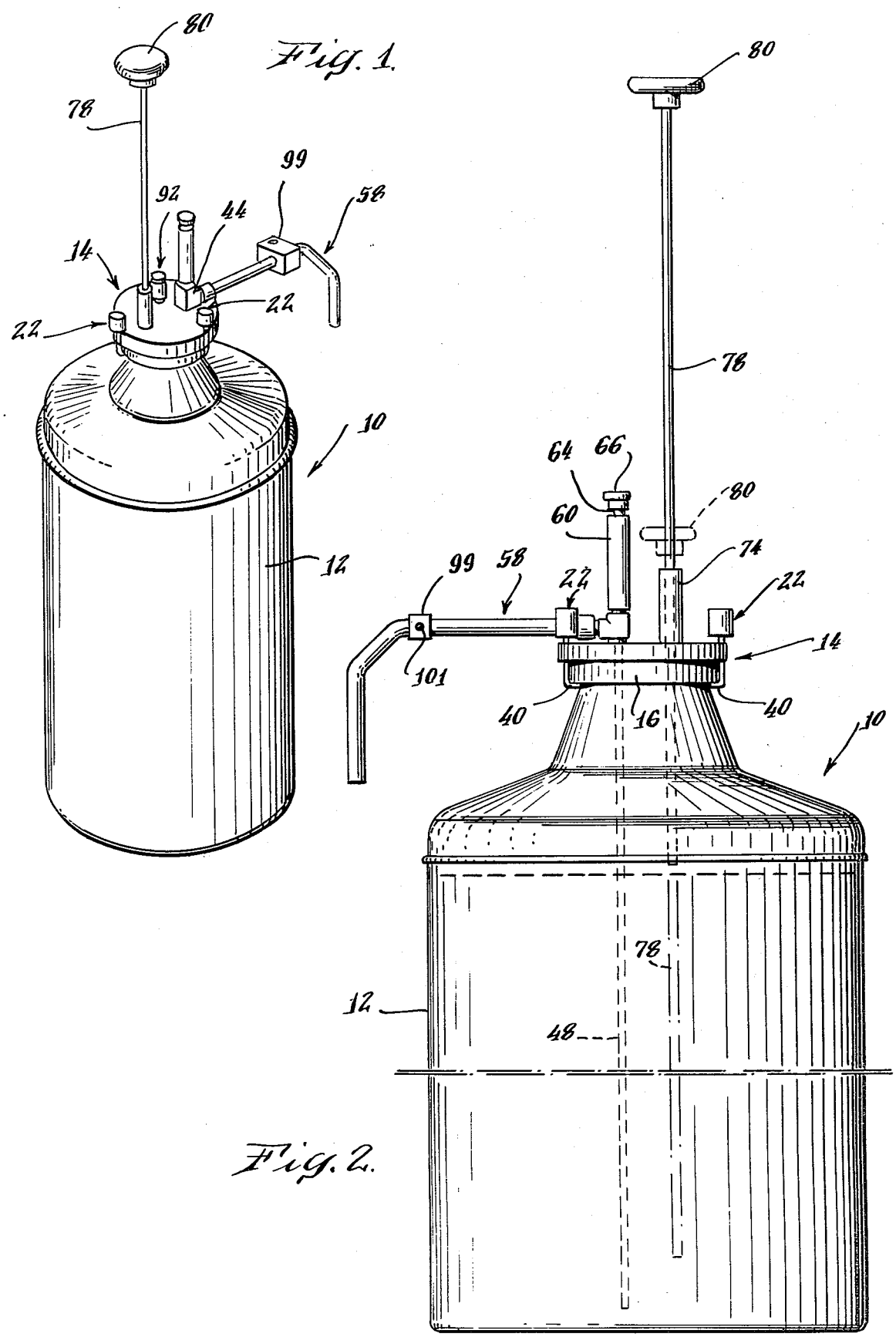

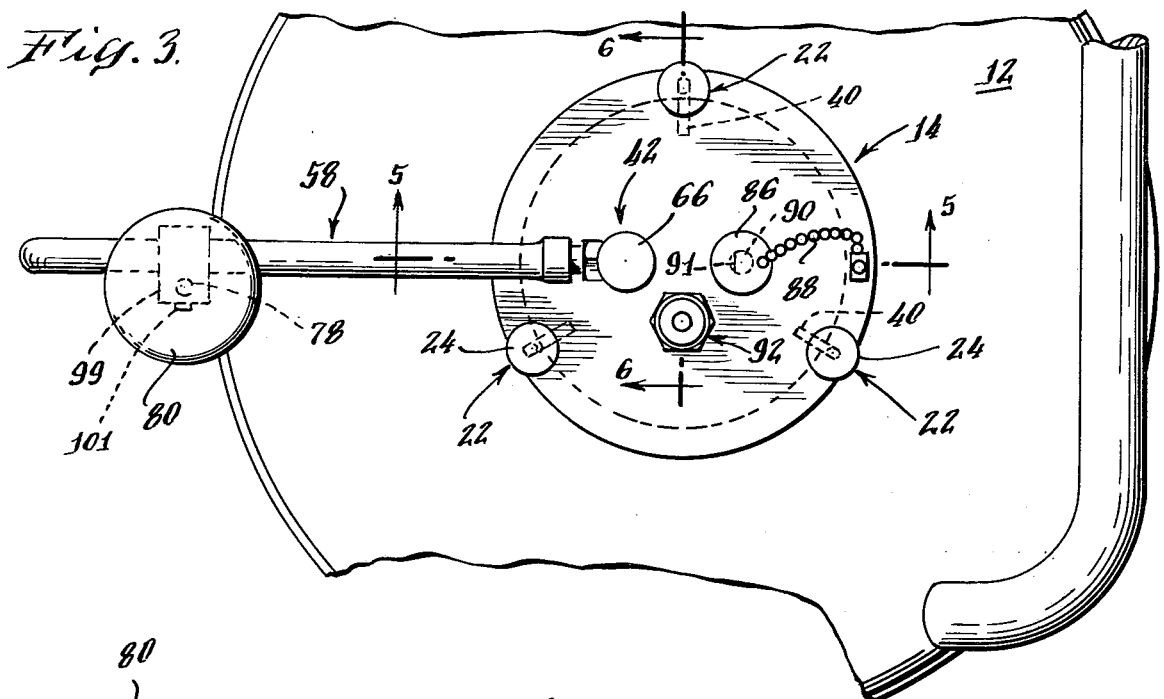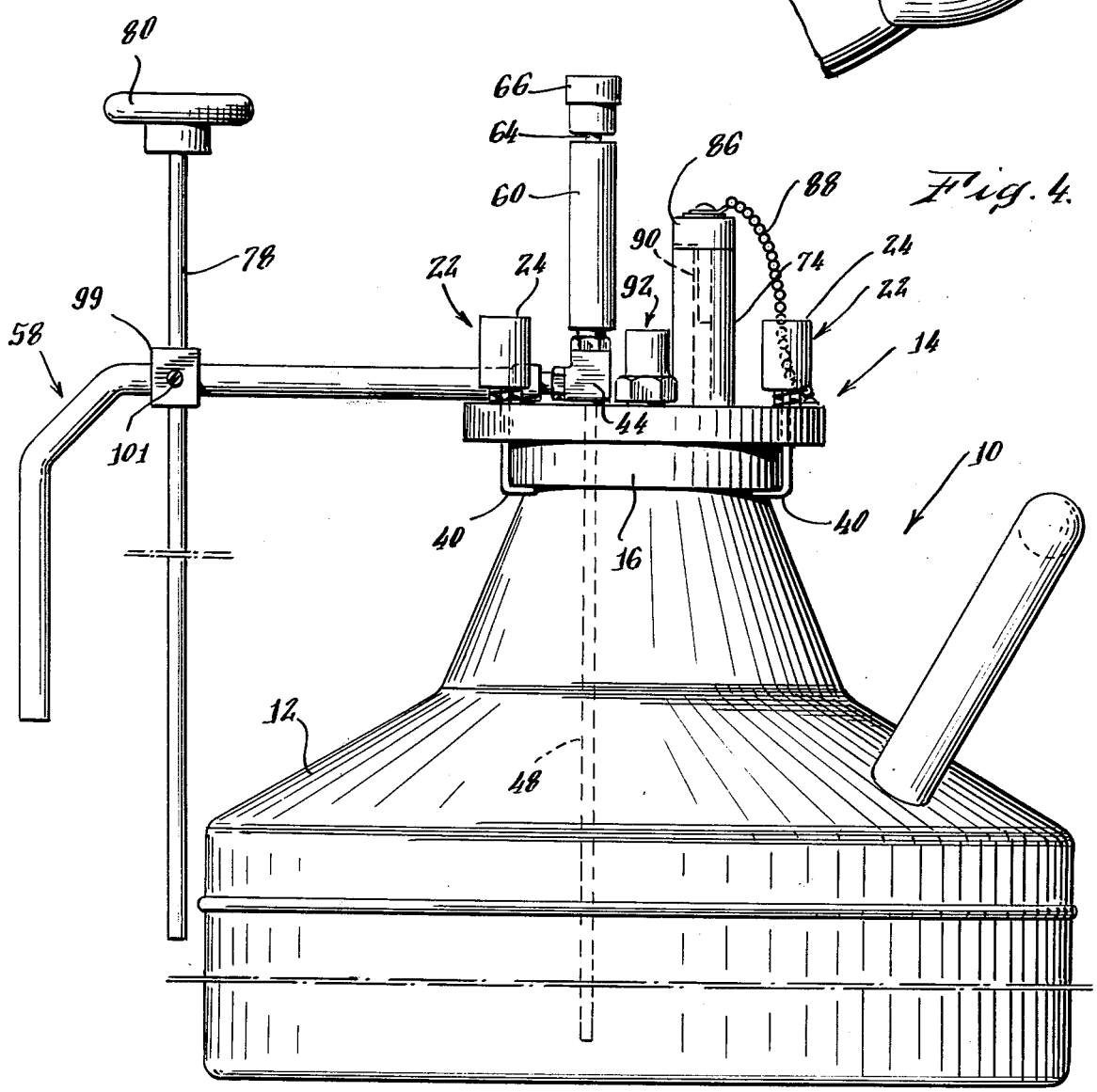

LIQUIFIED GAS WITHDRAWAL APPARATUS

BACKGROUND OF THE INVENTION

This invention relates to an apparatus used to withdraw liquified gas from a storage vessel or tank and to deliver the liquified gas to a smaller vessel from which it is dispersed in a spray, as for example, a cryosurgical instrument.

It has long been known to use liquified gas (such as helium, nitrogen, oxygen, air, freon, xenon, carbon dioxide, etc.) to freeze healthy or diseased tissue, and thereby necrotize the tissue. For instance, one well-known use of liquified gas is in the field of cryosurgery for the removal of lesions, both on the skin or internally. Usually, the object is to remove the lesion by destroying the tissue while maintaining adjacent portions of the tissue structure in place.

In such instruments the liquified gas is delivered through an insulated tube from a storage vessel or bottle to an applicator, where it is dispersed in a spray. Examples of such instruments are shown in U.S. Pat. Nos. 3,823,718; 3,534,739; and 3,702,114.

The apparatus of the present invention is used to charge the storage vessels or bottles of such instruments with a liquified gas refrigerant by withdrawing the refrigerant from a large tank supplied by a distributor or gas manufacturer and transferring it to the smaller storage vessel or bottle.

SUMMARY OF THE INVENTION

In accordance with the present invention, there is provided apparatus for pressurizing liquified gas in an enclosed reservoir tank and controlling the flow of the liquid from the reservoir through a delivery line connected to a spigot. The flow is controlled by an on-off valve disposed in the delivery line while selectively venting the pressurized vapor of the liquid generated above the reservoir. When flow is desired the valve is opened and a warm heat rod is slidable into and out of heat exchange relation with the coolant liquid in the reservoir, which causes the liquid to boil and consequently, increases the vapor pressure on the liquid to cause it to flow through the delivery line to the spigot. The length of the rod insertable in the liquid will control the boiling rate, and hence, vapor pressure on the liquid coolant.

BRIEF DESCRIPTION OF THE DRAWINGS

Further objects and advantages of the invention will become apparent from the following description and claims, and from the accompanying drawings, wherein:

FIG. 1 is a perspective view of the liquified gas withdrawal apparatus of the present invention;

FIG. 2 is a side view in elevation of the apparatus of FIG. 1;

FIG. 3 is a partial top plan view of the apparatus of FIG. 1;

FIG. 4 is a side view in elevation of the apparatus illustrated in FIG. 3 similar to that shown in FIG. 2, except with the heat rod used to increase the flow of liquid from the apparatus removed and a vent plug inserted in its stead;

DETAILED DESCRIPTION OF THE PREFERRED EMBODIMENT

Figure 5:
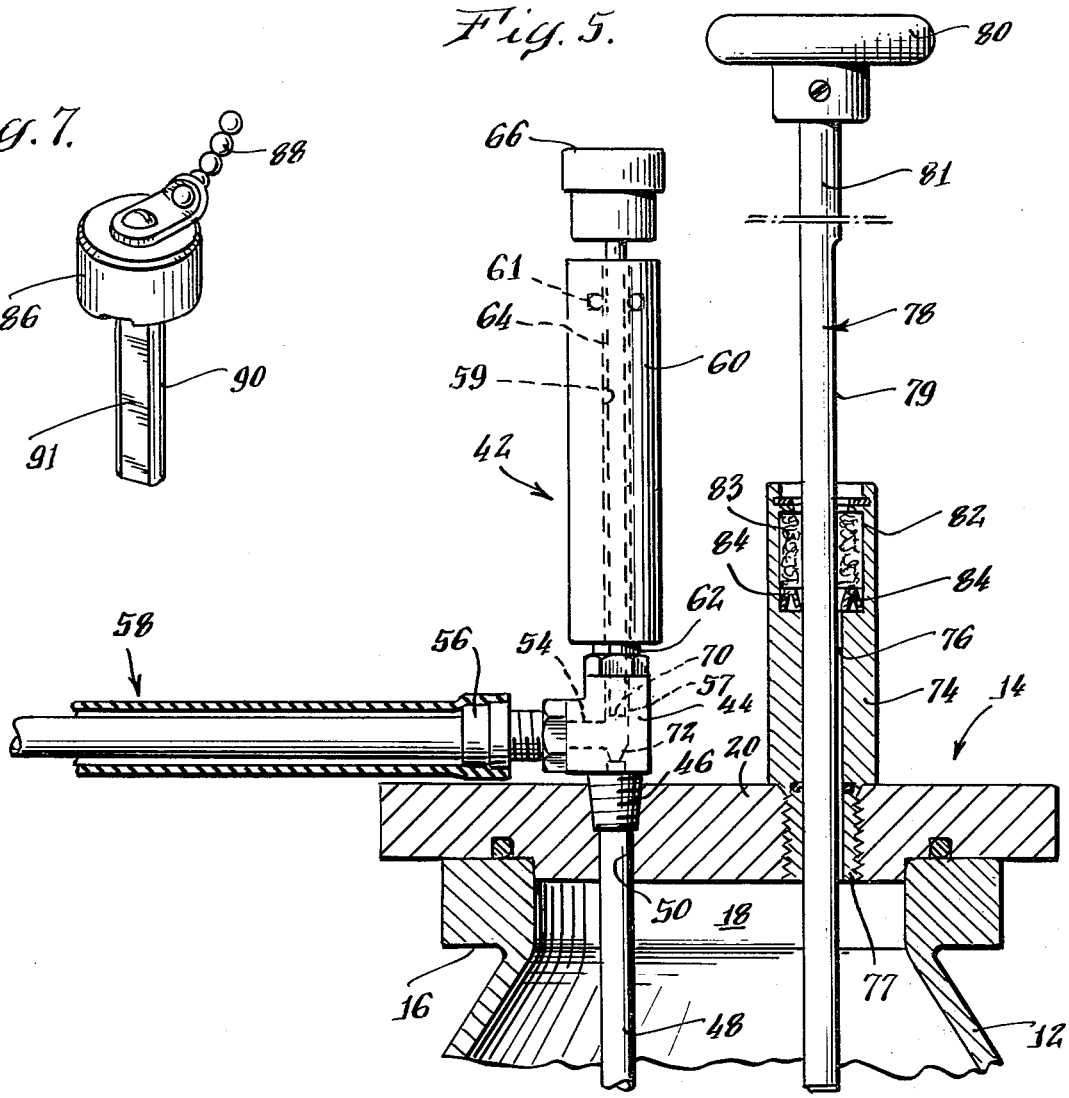
FIG. 5 is a cross-sectional view taken substantially along the plane indicated by line 5—5 of FIG. 3.
Figure 7:
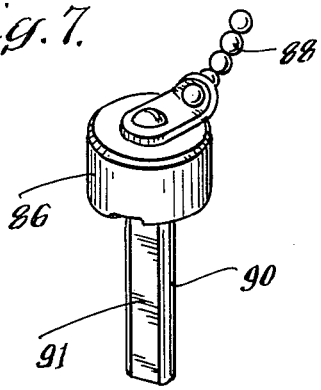
FIG. 7 is a perspective view of the vent plug used with the apparatus of the present invention.
Figure 6:
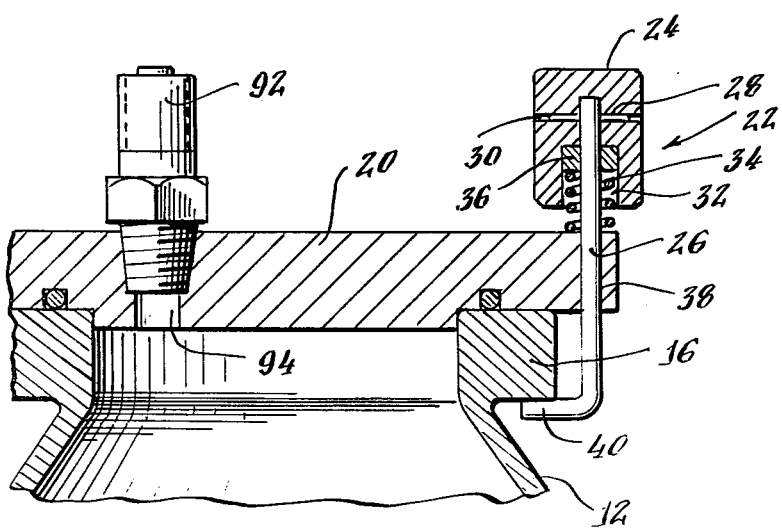
FIG. 6 is a cross-sectional view taken substantially along the plane indicated by line 6—6 of FIG. 3.

Referring now in detail to the drawings, wherein like numerals indicate like elements throughout the several views, the liquified gas withdrawal apparatus 10 of the present invention includes a large tank or insulated container 12 adapted to be filled with a liquid coolant, such as liquid nitrogen, by a gas distributor or manufacturer. Container 12 is provided with a cap assembly 14 adapted to be quickly connected and disconnected from seating engagement with an annular lip 16 extending about the mouth 18 of container 12. Cap assembly 14 includes an annular plate 20 receiving a plurality of quick connect-disconnect latches 22 at spaced locations about its circumference.

Latches 22 include a knob 24 receiving a L-shaped rod 26 held to knob 24 by a pin 28 received through one end of the rod in a cross bore 30 in knob 24. A coil spring 32 is received about rod 26 within a bore 34 in the underside of knob 24 and is adapted to abut a spacer 36 within bore 34. The median portion of L-shaped rod 26 is received through bores 38 spaced along the circumference of annular plate 20.

By depressing knob 24 against the force of coil spring 32, the distal end 40 of L-shaped rod 26 can be lowered relative to lip 16 of container 12. Rod 26 can be pivoted or rotated when lowered away from lip 16 so that the distal end 40 clears the bottom of lip 16. By similar rotation of all of the quick connect-disconnect latches 22, plate 20 can be removed from container 12 for servicing of the apparatus. Alternatively, by placing distal end 40 of each of the latches 22 beneath the bottom of lip 16 by rotating the same and allowing spring 32 to raise each of the distal horizontal ends 40 of each of the latches 22 into frictional engagement with the bottom of lip 16, tight sealing engagement is quickly attained between cap assembly 14 and container 12.

Connected to plate 20 is an extractor valve assembly generally designated by the numeral 42. Extractor valve assembly 42 includes an L-shaped pipe coupling 44 threadedly connected at one end 46 to plate 20. A liquid coolant delivery tube 48 extends downwardly from a bore 50 in plate 20 and cap assembly 14 beneath threaded end 46 of L-shaped pipe coupling 44 into the tank or container 12 adjacent the bottom thereof. Delivery tube 48 can be brazed to interior of end 46 of the L-shaped pipe connector 44.

The interior of liquid coolant delivery tube 48 is in communication with a passage 54 in the interior of L-shaped pipe connector 44, which is joined by a threaded connector 56 to a spigot assembly 58 for delivering liquid coolant to fill small cryosurgical instrument storage vessels or bottles. A second passage 57 within L-shaped pipe connector 44 is provided perpendicular to passage 54 and joins the interior of the delivery tube 48 to an elongated threaded bore 59 formed through an extractor valve sleeve 60. Sleeve 60 is threadedly coupled at 62 to the top of L-shaped pipe connector 44. Threadedly received within bore 59 of extractor sleeve 60 is an elongated valve element 64 connected to a knob 66. When knob 66 is rotated so that it is disposed adjacent to the top of sleeve 60, the distal end 70 of elongated valve element 64 will enter passage 57 and seat on an interior valve seat 72 within L-shaped pipe connector 44 to seal passage 54 leading to spigot assembly 58 against communication with the interior of delivery tube 48. In the position illustrated in FIG. 5, with knob 66 spaced from the top of element 64, passage 54 will be able to communicate with the interior of delivery tube 48 and the interior of tank 12. An O-ring seal 61 carried by element 64 seals bore 59, passage 57, delivery tube 48 and the interior of tank 12 to the atmosphere.

A heat rod and vent plug receiver tube 74 is also threadedly connected at a reduced diameter end 77 to plate 20 of cap assembly 14. Tube 74 includes an elongated bore 76 to slideably receive therethrough a heat rod 78 having a flat surface 79 throughout a part of its length for a purpose to be described. As shown in FIG. 2, heat rod 78 may be slideably inserted through sleeve 74 and plate 20 into the interior of tank or container 12 and into the liquid coolant reservoir disposed within the tank 12. Heat rod 78 includes a handle 80 at one end thereof permitting it to be pushed downwardly and raised relative to tank 12.

The upper end of tube 74 includes a widened portion 82 of bore 76 which houses a plurality of springs 84 in frictional contact with rod 78 to frictionally retain the rod 78 in an adjusted position relative to tank 12 as it is slid in and out of the tank, and to seal the bore 76, and the interior of tank 12 to the atmosphere when round portion 81 of the rod enters bore 76. Widened portion 82 includes packing material 83 in which springs 44 may be embedded to provide a guide for rod 78. When rod 78 is not in use, it can be removed from tube 74 and the sleeve capped by inserting a vent plug 86 secured to the cap assembly 14, and more particularly to plate 20 by a chain 88, into the interior of tube 74 in bore 76. Plug 86 includes a stem 90 having a flat surface 91 received in bore 76 in sleeve 74. The lower surface of cap 86 seats on top of sleeve 74. Because of flat 91, gas vapor generated in tank 12 can be vented to the atmosphere when plug 86 is inserted in bore 76 via bore 76, past flat 91, into bore 82 and to the atmosphere between the unsealed space between tube 74 and the cap of plug 86. Similarly, the flat 79 on rod 78 permits the venting of tank 12 as the rod 78 is removed from the tank when the flat 79 enters widened portion 82, precluding the vapor from exerting an exhorbitant amount of force on the rod as it is removed.

Plate 20 also has a relief valve 92 connected thereto which is in communication with the interior of tank 12 through plate assembly 20. The interior of valve 92 is in communication with the space above the reservoir containing the liquid coolant in insulated container 12 via a bore 94. Upon excess vapor pressure being generated within the interior of container 12, the pressure can be relieved by enabling the gas to escape through bore 94 into the interior of valve 92 wherein it is vented to the atmosphere through a suitable valve mechanism (not shown) well known to those of ordinary skill in the art contained within valve 92; for example, a one-way check valve. This valve can consist of a spring-biased ball valve, wherein the valve opens when the vapor within valve 92 exceeds the pressure exerted by the spring against the ball to close the opening venting the valve to the atmosphere.

In use, in order to extract liquid coolant through spigot assembly 58 from the interior of tank 12, knob 66 and rod 64 are unthreaded in bore 59 to unseat end 70 from valve seat 72 to permit communication of tube 48 with spigot assembly 58 through passage 54. Vapor generated above the liquid coolant in tank 12 will cause liquid coolant to flow up delivery tube 48 through passage 54 and out spigot assembly 58. The flow rate of the liquid coolant through delivery tube 48 and spigot assembly 58 is controlled by inserting heat rod 78 through bore 76 into a contact with the liquid coolant in tank 12 causing the rod 78, which is at ambient temperature, to boil the liquid coolant to form vapor to push the liquid coolant up through delivery tube 48. Depending upon the length of the rod 78 disposed within the liquid coolant, the rate can be effectively controlled. Springs 84 retain the rod in an adjusted position and when placed in contact with the round portion 81 of the rod, seal the tank 12 to the atmosphere.

Valve 64 is then closed by rotating rod 66 until end 70 is seated on valve seat 72, precluding communication of the interior of tube 48 with spigot assembly 58, and rod 78 is removed from tank 12 and tube 74. Upon removal of rod 78 from the interior of tank 12 the vent plug 86 is seated on top of tube 74. Vapor can then be vented to the atmosphere through bore 76 thus precluding further pressure on liquid coolant within tank 12 to shut down the liquid withdrawal system.

When rod 78 is removed from bore 76, it can conveniently be stored in a hole in a block 99 carried by spigot assembly 58. A set screw 101 can retain the rod in the block 99.

What is claimed as new is as follows:

1. Liquified gas withdrawal apparatus for removing liquified gas coolant from an enclosed reservoir adapted to receive a quantity of said liquified gas coolant, said apparatus comprising:
   a delivery tube having one end adapted to be immersed in the liquified gas coolant within said reservoir and capable of conducting the coolant outwardly of said reservoir;
   means for selectively pressurizing said reservoir in the presence of the coolant to thereby force coolant along said delivery tube, said means including reciprocable rod means selectively slidable in heat exchange relation into and out of said reservoir for contact with said liquified gas coolant to increase the boiling rate of said coolant and build up pressure in said reservoir;
   valve means in communication with said delivery tube for selectively blocking the other end of said delivery tube to prevent conduction of said coolant from said reservoir; and
   vent means normally open to the atmosphere in communication with the space above the level of coolant in said reservoir, said reciprocable rod means being received within said vent means to close said vent means to the atmosphere when said rod means is selectively slidable in heat exchange relation into and out of said reservoir.

2. The apparatus of claim 1 wherein said delivery tube, valve means, and vent means are all fixed to a single platform received on said reservoir.

3. The apparatus of claim 2 including quick connect-disconnect means carried by said platform for attaching said platform to said reservoir.

4. The apparatus of claim 1 wherein said valve means includes
   a L-shaped pipe connector between said delivery tube and a sleeve having an elongated bore therethrough,
   a rod threadedy received in the bore of said sleeve having a distal end adapted upon threading of said rod into said sleeve to block communication of said delivery tube with the atmosphere.

5. The apparatus of claim 1 wherein said delivery tube includes means for holding said reciprocable rod means when not inserted in said vent means.

6. The apparatus of claim 1 wherein said vent means includes an elongated tube providing communication between the atmosphere and said reservoir, said tube including an elongated bore therethrough, cap means including a downwarding extending plug received within said bore, said cap means having a flat side permitting coolant vapor to escape from said reservoir means through said bore means past said cap means.

7. The apparatus of claim 1 wherein said reciprocable rod means includes a flat surface along the length thereof.

* * * * *